United States Patent
Tolmachev et al.

(10) Patent No.: US 6,954,560 B2
(45) Date of Patent: Oct. 11, 2005

(54) ATTENUATED TOTAL REFLECTION SPECTROSCOPIC ANALYSIS OF ORGANIC ADDITIVES IN METAL PLATING SOLUTIONS

(75) Inventors: Yuriy V. Tolmachev, Woodridge, IL (US); Mackenzie King, Southbury, CT (US)

(73) Assignee: Advanced Technology Materials, Inc., Danbury, CT (US)

(*) Notice: Subject to any disclaimer, the term of this patent is extended or adjusted under 35 U.S.C. 154(b) by 289 days.

(21) Appl. No.: 10/331,396

(22) Filed: Dec. 30, 2002

(65) Prior Publication Data

US 2004/0126049 A1 Jul. 1, 2004

(51) Int. Cl.[7] ............................................. G02B 6/00
(52) U.S. Cl. ........................................................ 385/12
(58) Field of Search ........................... 385/12, 123–131, 385/140, 902; 204/408, 416, 434; 205/81, 788.5, 789.5; 356/431–441, 402–425

(56) References Cited

U.S. PATENT DOCUMENTS

| | | | | |
|---|---|---|---|---|
| 4,818,710 A | * | 4/1989 | Sutherland et al. | ......... 436/527 |
| 4,829,186 A | * | 5/1989 | McLachlan et al. | ........ 250/373 |
| 4,851,665 A | * | 7/1989 | Pesavento et al. | .......... 356/412 |
| 5,434,411 A | | 7/1995 | Miyahara et al. | ...... 250/339.07 |
| 2003/0127341 A1 | * | 7/2003 | King et al. | .............. 205/788.5 |
| 2004/0040842 A1 | * | 3/2004 | King et al. | ................. 204/408 |

OTHER PUBLICATIONS

Paul A. Wilks, "Infrared Solves Some Unusual Problems for the Film Industry", Spectroscopy, Dec. 2002, 116, 17(12).

Volker Thomsen, "Walther Gerlach and the Foundations of Modern Spectrochemical Analysis", Spectroscopy, Dec. 2002, 117, 17(12).

Said Al Mosheky, et al., "In Situ Real–Time Monitoring of a Fermentation Reaction Using a Fiber–Optic FT–IR Probe".

* cited by examiner

Primary Examiner—Frank G. Font
Assistant Examiner—Christopher M. Kalivoda
(74) Attorney, Agent, or Firm—Steven J. Hultquist; Intellectual Property/Technology Law; Margaret Chappuis

(57) ABSTRACT

The present invention relates to method and apparatus for determining concentrations of organic additives in metal plating solutions, based on infrared spectroscopy, and more specifically attenuated total reflection infrared spectroscopy (ATR-IR).

6 Claims, 3 Drawing Sheets

ATTENUATED TOTAL REFLECTION SPECTROSCOPIC ANALYSIS OF ORGANIC ADDITIVES IN METAL PLATING SOLUTIONS

BACKGROUND OF THE INVENTION

1. Field of the Invention

The present invention relates to a method and apparatus for determining concentrations of organic additives in metal plating solutions, based on spectroscopy, and more specifically attenuated total reflection (ATR) spectroscopy.

2. Background of the Invention

The recent switch from aluminum to copper interconnects in semiconductor industry has lead to the development of a large variety of new copper plating solutions containing various organic additives, including suppressor, accelerator, and leveler. The finer scale of the metal patterning and the use of automatic manufacturing techniques demand a faster and more precise control of the composition of the metal plating solution, especially with respect to the concentrations of the organic additives in such metal plating solution, which have significant impact upon the quality of the metal finish layer. Current analytical techniques used for the process control in metal plating, such as chromatography and electro-potentiometry, are time-consuming and expensive, and lack selectivity for specific organic additive species.

It is an object of the present invention to provide an analytical method and apparatus for determining the organic additive concentration in metal plating solutions, which is less time-consuming, requiring minimal or no sample preparation, and having excellent selectivity and sensitivity for specific organic additive species.

Other objects and advantages will be more fully apparent from the ensuing disclosure and appended claims.

SUMMARY OF THE INVENTION

The present invention relates in one aspect to a method for determining concentration of one or more organic additives in a sample metal plating solution, comprising the steps of providing radiation energy to the sample metal plating solution, detecting absorbance of the radiation energy by such metal plating solution, and determining the concentration of one or more organic additive species in such metal plating solution, based on absorbance spectrum that is characteristic to such one or more target organic additive species.

Specifically, an attenuated total reflection spectroscopic technique is employed, by providing an optical waveguide having a refraction index that is higher than that of the sample metal plating solution and placing the optical waveguide adjacent to the metal plating solution to form an interface between such optical waveguide and such metal plating solution. The radiation energy propagates from the optical waveguide toward the metal plating solution in such a manner that such radiation energy is reflected back into the optical waveguide by such interface, and wherein attenuation of the radiation energy is measured for determining the concentration of one or more organic additives in the sample metal plating solution.

The present invention in another aspect relates to an analytical apparatus for determining concentration of one or more organic additives in a sample metal plating solution, comprising:

(a) an analytical cell comprising a liquid inlet, a sample solution holder, and a liquid outlet, wherein the sample metal plating solution is passed into the analytical cell via the liquid inlet, wherein the sample solution holder comprises a front wall and a back wall placed in close proximity so as to hold the sample metal plating solution in form of a liquid film;

(b) an irradiation light source for irradiating light onto the liquid film;

(c) a light detector for detecting light transmitted or emitted by the liquid film; and (d) a computational device connected with the light detector, for determining concentration of one or more organic additive species contained by such sample metal plating solution, based on absorbance of the irradiated light by the sample metal plating solution.

The term "computational device" used herein includes any electronic and/or digital devices having computational functions, including but not limited to microprocessors, calculators, personal computers, workstations, etc.

A further aspect of the present invention relates to an analytical apparatus for determining concentration of one or more organic additives in a sample metal plating solution, comprising:

(a) an analytical cell comprising a sample solution holder having first and second walls, wherein the first and second walls are placed in close proximity so as to hold the sample metal plating solution in form of a liquid film, and wherein at least one of the first and second walls comprises solid crystal material having a refraction index that is higher than that of the sample metal plating solution;

(b) an irradiation energy source for irradiating radiation energy onto such at least one of the first or the second walls, in such a manner that the radiation energy travels within such at least one of the first or the second walls via multiple internal reflections;

(c) an optical detector for detecting the radiation energy after the multiple internal reflections and for determining total attenuation of the radiation energy after the multiple internal reflections; and (d) a computational device connected with the optical detector, for determining concentration of such one or more organic additive species contained by the sample metal plating solution, based on the total attenuation of the radiation energy.

A still further aspect of the present invention relates to an analytical apparatus for determining concentration of one or more organic additives in a sample metal plating solution, comprising:

(a) a fiber optic tip probe comprising a fiber optic tip immerged in the sample metal plating solution, wherein the fiber optic tip has a refraction index that is higher than that of the sample solder plating solution;

(b) a radiation energy source for irradiating radiation energy onto the fiber optical tip, in such a manner that the radiation energy propagates within the fiber optical tip and is reflected back by an interface between the fiber optical tip and the surrounding metal plating solution;

(c) an optical sensor connected to the fiber optical tip probe for detecting the reflected radiation energy and measuring attenuation of said radiation energy; and (d) a computational device connected with the optical detector, for determining concentration of one or more organic additive species contained by such sample metal plating solution, based on the attenuation of the radiation energy measured by the optical sensor.

Additional aspects, features and embodiments of the invention will be more fully apparent from the ensuing disclosure and appended claims.

DETAILED DESCRIPTION OF THE INVENTION AND PREFERRED EMBODIMENTS THEREOF

The analysis of organic additive concentration in a metal plating solution can be conducted using spectroscopy, wherein a light sensitive detector is constructed and arranged for detecting light absorbance of the metal plating solution, and wherein the characteristic absorbance of one or more target organic additive species in such solution is used for determining the concentration of such target organic additive species in such metal plating solution.

Infrared spectroscopy is particularly preferred for detecting the organic additives in the metal plating solution, since organic compounds have sharp and relatively narrow absorption peaks in the infrared region, which are especially suitable for qualitative and quantitative absorbance analysis. In the performance of a direct infrared spectroscopic analysis, an infrared light beam is passed across a thin film formed of the sample metal plating solution, and the transmitted infrared light is measured as a function of wavelength, which yields a characteristic spectrum. The measurement may be direct, yielding an absorption spectrum; alternatively, the measurement may be indirect, yielding an emission spectrum.

Although infrared spectroscopy is a preferred embodiment in the present invention, such preference does not limit the broad scope of the present invention in any manner, and radiation of shorter wavelength, such as visible light or ultraviolet light, can also be used for the spectroscopic analysis of the organic additive concentration in the metal plating solution.

Figure 1:
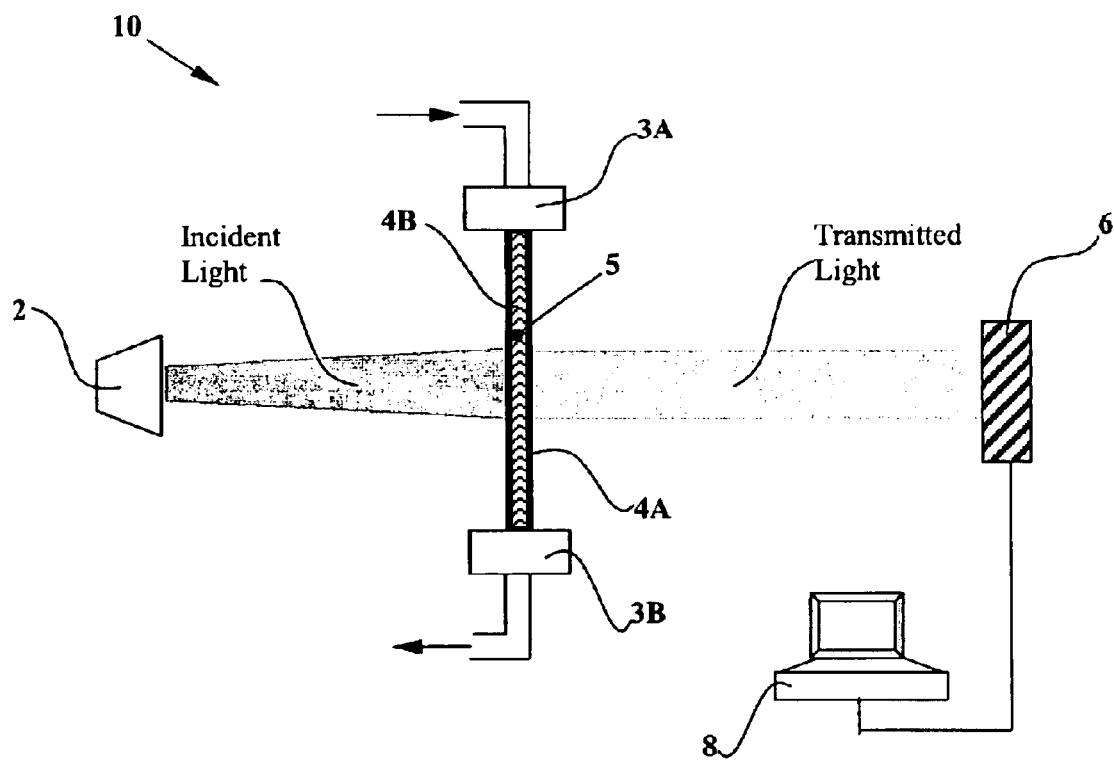
FIG. 1 shows a perspective view of a spectroscopy-based metal plating solution analyzer, which measures the characteristic absorption spectrum of light by a thin film form of the sample metal plating solution for determining concentration of organic additives therein.

Specifically, FIG. 1 shows an analytical apparatus 10, according to one embodiment of the present invention, which comprises an analytical cell with a liquid inlet manifold 3A, a sample solution holder, and a liquid outlet manifold 3B. The sample solution holder receives a sample metal plating solution from the liquid inlet manifold 3A and discharges such into the liquid outlet manifold 3B, while such sample solution holder has a front wall 4A and a back wall 4B in close proximity to each other, so as to hold the sample metal plating solution in form of a sufficiently thin liquid film 5. An irradiation light source 2 is provided for irradiating light onto the liquid thin film 5. The irradiating light includes, but is not limited to, infrared light, ultraviolet light, visible light, etc. Such irradiating light preferably is infrared (IR) light. A photodiode 6 is provided for detecting light transmitted or emitted by the liquid thin film 5, and preferably the photodiode 6 is IR-sensitive. The photodiode 6 is connected to a computational device 8, so that characteristic absorbance data of specific organic additive species in the sample metal plating solution can be collected and sent to such computational device 8 for concentration determination. Such absorbance-based concentration determination is quick, and can be used for continuous and non-intrusive measurement of the metal plating solution, while measured sample solution can still be used for subsequent plating.

Accuracy of the above-described direct infrared spectroscopic analysis, when employed to analyze aqueous solutions such as metal plating solutions, may be improved by separating the organic components from the water component of the metal plating solution, since water demonstrates a strong absorption for infrared light. Useful separation techniques include but are not limited to extraction and spray drying.

The present invention in another embodiment employs attenuated total reflection (ATR) spectroscopy, which is based on the attenuation of evanescent waves propagating at the interface between an optical waveguide of a higher refraction index and the metal plating solution of a lower refraction index. Specifically, the phenomenon of total internal reflection of incident light is observed when such light propagates from the optical waveguide of higher refraction index to the metal plating solution of lower refraction index, if the incident angle of such light is larger than a critical value. When total internal reflection occurs, the incident light does not pass into the metal plating solution (i.e., there is no refraction ray), but is reflected back into the optical waveguide by the interface between the optical waveguide and the metal plating solution. Therefore, the light can travel inside the optical waveguide for a long distance, through multiple internal reflections.

However, at each internal reflection, the light actually penetrates through the interface between the optical waveguide and the metal plating solution into the metal plating solution, at a very short distance (e.g., ~1 $\mu$m), and therefore generates an evanescent wave in the metal plating solution with a short penetration depth (i.e., ~1 $\mu$m). If the metal plating solution comprises no absorbing species, the light reflected by the interface is 100% of the incident light, but if the metal plating solution does comprise an absorbing species (e.g., the organic additives), the light reflected by the interface is attenuated in comparison to the incident light, and the difference in the intensity of the incident light and the reflected light (i.e., the attenuation) can be used for determining the types and concentration of the absorbing species in the metal plating solution.

Such attenuated total reflection (ATR) spectroscopic method can use ultra-violet light, visible light, or infrared light, as long as the appropriate optical waveguide is provided. ATR spectroscopy in the mid-infrared region is particularly preferred for analyzing the organic additive concentration in metal plating solutions in the present invention, for reasons mentioned hereinabove.

When attenuation for each internal reflection is very small and difficult to measure, such attenuation can be increased via multiple reflections along the length of the optical waveguide. The Fourier transform (FT) technique is particularly suitable for making the ATR spectroscopic measurements, due to its multiplex advantages.

Figure 2:
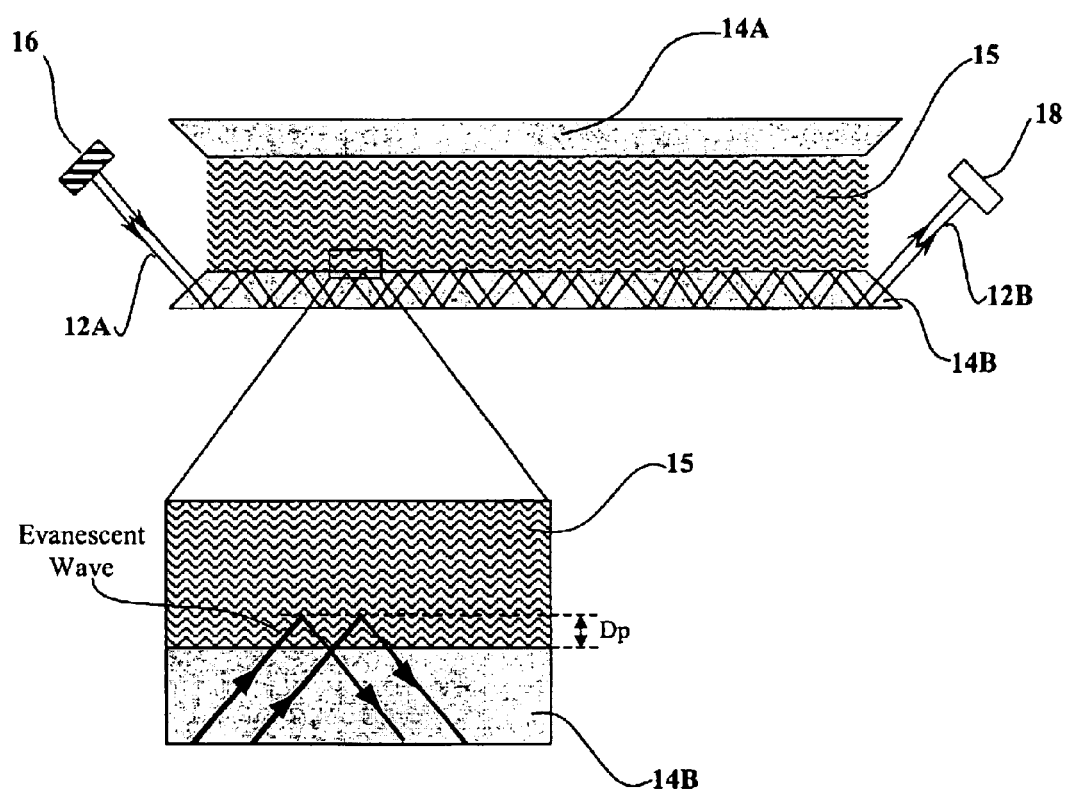
FIG. 2 shows a part of a metal plating solution analyzer according to one embodiment of the present invention, which uses the attenuated total reflection (ATR) spectroscopic analytical method for determining the organic additive concentration in metal plating solutions.

FIG. 2 shows a perspective view of a part of a metal plating solution analyzer according to one embodiment of the present invention, which uses the above-described attenuated total reflection (ATR) spectroscopic analytical method for determining the organic additive concentration in metal plating solutions.

Specifically, such a metal plating solution analyzer comprises a sample solution holder, having a first wall 14A and a second wall 14B in close proximity to each other, so as to hold a sample metal plating solution in form of a sufficiently thin liquid film 15. At least one of the first and second walls 14A and 14B, comprises an internal reflection element (IRE), which is a solid crystal material having a refraction index of at least 1.5, such as zinc selenide (ZnSe) and germanium (Ge). Preferably, both the first and second walls 14A and 14B comprise an IRE as well as fiber optic materials, which form optical waveguides for the incident light beam 12A (to simplify the drawings, the incident light beam 12A is only provided for the second wall 14B in FIG. 2, but in reality, either one or both of walls 14A and 14B can be used as optical waveguides for the incident light beam).

The light source 16, preferably an infrared light source, provides at least one pulse of radiation, in form of an incident light beam 12A, which travels inside the second wall 14B through multiple internal reflections and is detected by an optical sensor 18, preferably an infrared-sensitive optical sensor, at the other side of the second wall 14B. During each internal reflection, the light beam penetrates through the interface between the second wall 14B and the sample metal plating solution 15 at a very short distance Dp to form an evanescent wave in the sample metal plating solution 15. The evanescent wave so formed is absorbed by the organic additive species in the metal plating solution 15 and leads to attenuation of the incident light beam, which can be detected by the optical sensor 18 and used for determination of the organic additive concentration in the metal plating solution 15.

The absorption spectrum generated by the metal plating solution, in response to the single pulse of light radiation, consists primarily of the characteristic absorption information of the metal plating solution, which is similar to the transmission spectrum of the metal plating solution generated by the analytical apparatus 10 of FIG. 1, but with stronger and more reliable analytical signals.

To further improve the analytic signal, the first and/or second walls 14A and 14B comprising the solid crystal material may be coated with a thin metal film, such as gold. The metal film serves to enhance the signal at the interface between the metal plating solution and the solid crystal material. This is similar in concept to surface enhanced Raman spectroscopy and works from the same principles.

Figure 3:
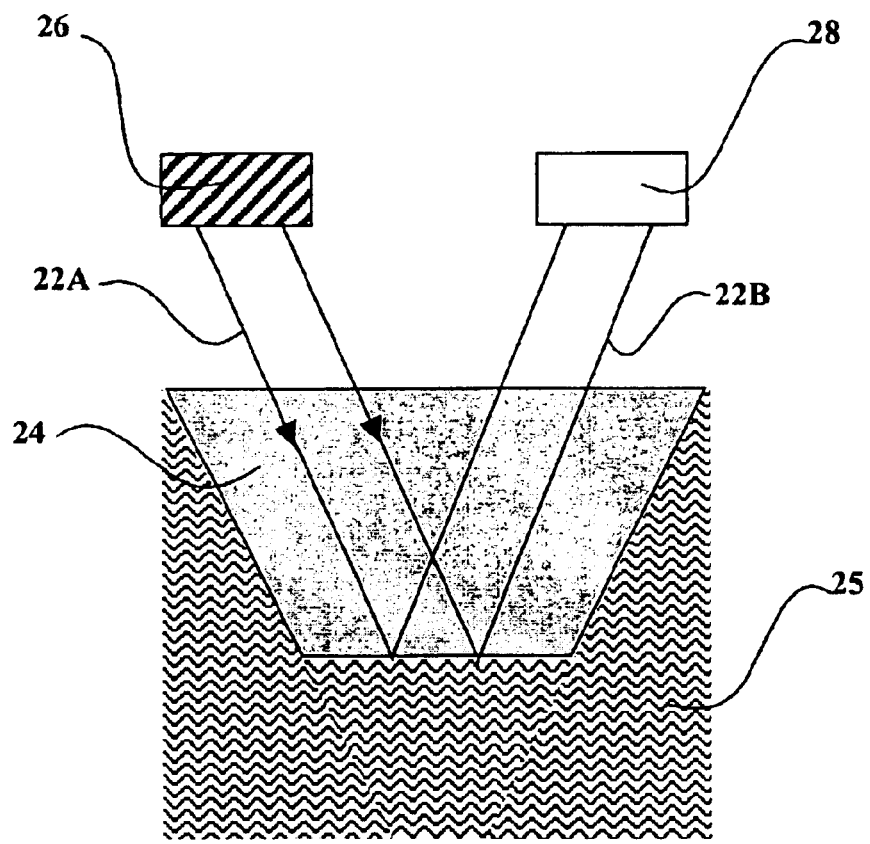
FIG. 3 shows a part of a fiber optical tip probe according to one embodiment of the present invention, which can be used for the ATR spectroscopic analysis of the metal plating solutions.

In a further embodiment, a fiber optical tip probe as shown in FIG. 3 can be used for analyzing a sample metal plating solution. Such fiber optical tip probe comprises a fiber optical tip 24, which can be immersed into the sample metal plating solution 25. The fiber optical tip probe is connected to a light source 26 that provides incident light beam 22A. The incident light beam 22A propagates within the fiber optical tip 24 and is reflected back by the interface between the fiber optical tip 24 and the surrounding metal plating solution 25. A optical sensor 28 connected to the fiber optical tip probe detects the reflected light beam 22B and measures the light attenuation of such reflected light beam 22B in comparison to the incident light beam 22A, to provide characteristic absorbance information for determining the organic additive concentration in the sample metal plating solution 25.

Preferably the fiber optical tip probe as shown in FIG. 3 has an ATR crystal attached to the fiber optical tip probe. In such a case, the ATR fiber optical tip probe may be immersed into the sample metal plating solution 25 for real-time, on-line analysis of the organic components of the metal plating solution.

The absorbance measurement of the sample metal plating solution can be compared to that of one or more standard metal plating solutions containing organic additives of known concentration, so as to determine the organic additive concentration in the sample metal plating solution.

Preferably, the characteristic absorbance of the sample metal plating solution is first measured, using the ATR techniques described hereinabove, and recorded, and successive standard additions of organic additives are subsequently introduced to the sample metal plating solution in various combinations, while the characteristic absorbance of the sample metal plating solution is measured and recorded after each standard addition. Multiple point regression analysis is then carried out to extrapolate the initial organic additive concentration in the sample plating solution, before introduction of any standard additions.

The method and apparatus of the present invention as described herein allow organic additive analysis to be completed within a few minutes. They require minimal or no sample preparation, and demonstrate excellent selectivity and sensitivity. Moreover, they can be easily adapted to different types of metal plating baths and can be performed automatically. More importantly, the organic additive analysis using such method and apparatus is non-invasive, i.e., the sample metal plating solution can be used for subsequent plating after such analysis, and therefore reducing sample consumption to a minimum.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. A method for determining concentration of one or more organic additive species in a sample metal plating solution, comprising the steps of providing an optical waveguide having a refraction index that is higher than that of the sample metal plating solution and placing said optical waveguide adjacent to the metal plating solution to form an interface between said optical waveguide and said metal plating solution, providing infrared light so that the infrared light propagates from the optical waveguide to said sample metal plating solution and is reflected back into said optical waveguide by said interface thereby effectuating attenuated total reflection of the infrared light in said optical waveguide, measuring attenuation of the infrared light, and determining concentration of said one or more organic additive species in said metal plating solution, based on the measured attenuation of the infrared light.

2. The method of claim 1, wherein the infrared light is reflected multiple times inside said optical waveguide and wherein total attenuation of the infrared light after multiple internal reflections is measured for determining the concentration of said one or more organic additive species in the sample metal plating solution.

3. The method of claim 1, wherein:

(a) an analytical cell comprising a sample solution holder having a first wall and a second wall is provided, (b) the fist and second walls are placed in close proximity so as to hold the sample metal plating solution in form of a liquid film, (c) at least one of the first and second walls comprises solid crystal material having a refraction index that is higher than that of the sample metal plating solution, (d) an infrared light source is provided for irradiating infrared light onto said at least one of the first and the second walls, in such a manner that the infrared light travels within said at least one of the first and the second walls via multiple internal reflections, (e) an optical detector is provided for detecting the infrared light after the multiple internal reflections and for determining total attenuation of the infrared light after said multiple internal reflections, and (f) a computational device is connected with the optical detector, for determining concentration of said one or more organic additive species contained by said sample metal plating solution, based on the total attenuation of the infrared light.

4. The method of claim 1, wherein:

(a) a fiber optic tip probe comprising a fiber optic tip is provided and immersed in the sample metal plating solution, wherein said fiber optic tip has a refraction index that is higher than that of the sample metal plating solution, (b) an infrared light source is provided for irradiating infrared light onto the fiber optical tip, (c) the infrared light propagates within the fiber optical tip in such manner that it is reflected back by an interface between the fiber optical tip and the surrounding metal plating solution, (d) an optical sensor is connected to the fiber optical tip probe for detecting the reflected infrared light and measuring attenuation of said infrared light, and (e) a computational device is connected with the optical sensor, for determining concentration of said one or more organic additive species contained by said sample metal plating solution, based on the attenuation of the infrared light measured in step (d).

5. An analytical apparatus for determining concentration of one or more organic additive species in a sample metal plating solution, comprising:

(a) an analytical cell comprising a sample solution holder having a first wall and a second wall, wherein the first and second wall are placed in close proximity so as to hold the sample metal plating solution in form of a liquid film, and wherein at least one of the first and second walls comprises solid crystal material having a refraction index that is higher than that of the sample metal plating solution;

(b) an infrared light source for irradiating infrared light onto said at least one of the first and the second walls to effectuate attenuated total reflection therein, in such a manner that the infrared light travels within said at least one of the first and the second walls via multiple internal reflections;

(c) an optical detector for detecting the infrared light after the multiple internal reflections and for determining total attenuation of the infrared light after said multiple internal reflections; and (d) a computational device connected with the optical detector, for determining concentration of said one or more organic additive species contained by said sample metal plating solution, based on the total attenuation of the infrared light.

6. An analytical apparatus for determining concentration of one or more organic additive species in a sample metal plating solution, comprising:

(a) a fiber optic tip probe comprising a fiber optic tip immersed in the sample metal plating solution, wherein said fiber optic tip has a refraction index that is higher than that of the sample plating solution;

(b) an infrared light source for irradiating infrared light onto the fiber optical tip to effectuate attenuated total reflection of the infrared light therein, in such a manner that the infrared light propagates within the fiber optic tip and is reflected back by an interface between the fiber optic tip and the surrounding metal plating solution;

(c) an optical sensor connected to the fiber optical tip probe for detecting the reflected infrared light and measuring attenuation of said infrared light; and (d) a computational device connected with the optical sensor, for determining concentration of said one or more organic additive species contained by said sample metal plating solution, based on the attenuation of the infrared light measured by the optical sensor.

* * * * *